US009911666B2

(12) United States Patent
Chin et al.

(10) Patent No.: US 9,911,666 B2
(45) Date of Patent: Mar. 6, 2018

(54) APPARATUS AND METHOD FOR INSPECTING A SEMICONDUCTOR PACKAGE

(71) Applicant: SAEDGE VISION SOLUTIONS PTE. LTD., Singapore (SG)

(72) Inventors: Ah Kow Chin, Singapore (SG); Choong Fatt Ho, Singapore (SG); Victor Vertoprakhov, Singapore (SG); Soon Wei Wong, Singapore (SG)

(73) Assignee: SAEDGE VISION SOLUTIONS PTE. LTD., Singapore (SG)

( * ) Notice: Subject to any disclaimer, the term of this patent is extended or adjusted under 35 U.S.C. 154(b) by 0 days.

(21) Appl. No.: 15/036,011

(22) PCT Filed: Nov. 10, 2014

(86) PCT No.: PCT/SG2014/000527
§ 371 (c)(1),
(2) Date: May 11, 2016

(87) PCT Pub. No.: WO2015/069191
PCT Pub. Date: May 14, 2015

(65) Prior Publication Data
US 2016/0254199 A1 Sep. 1, 2016

(30) Foreign Application Priority Data
Nov. 11, 2013 (SE) .................................. 2013084975

(51) Int. Cl.
| G01N 21/00 | (2006.01) |
| H01L 21/66 | (2006.01) |
| H01L 23/00 | (2006.01) |
| G01N 21/88 | (2006.01) |
| G01N 21/952 | (2006.01) |
| H01L 21/67 | (2006.01) |
| G01N 21/95 | (2006.01) |

(52) U.S. Cl.
CPC ......... H01L 22/14 (2013.01); G01N 21/8851 (2013.01); G01N 21/9501 (2013.01);
(Continued)

(58) Field of Classification Search
CPC .. G01N 33/505; G01N 21/8851; G01N 21/95; G01N 21/9501; G01N 21/952;
(Continued)

(56) References Cited

U.S. PATENT DOCUMENTS 5,138,180 A * 8/1992 Yamanaka ............... H01L 24/78
250/559.07
5,225,891 A * 7/1993 Choumei ........... G01N 21/8806
348/126
(Continued)

FOREIGN PATENT DOCUMENTS

EP 1830176 9/2007

OTHER PUBLICATIONS

International Search Report and Written Opinion dated May 11, 2015, PCT Patent Application No. PCT/SG2014/000527 filed Nov. 10, 2014, Australian Patent Office.

*Primary Examiner* — Michael P Stafira
(74) *Attorney, Agent, or Firm* — Mannava & Kang, P.C.

(57) ABSTRACT

There is provided an apparatus and method for inspecting a semiconductor package. The apparatus includes at least one 3D camera positioned at a first angle relative to a normal axis of the semiconductor package; and a light source configured to provide illumination for the at least one 3D camera, the light source being directed at the semiconductor package. The method includes casting a shadow of a bonded wire onto the semiconductor package; obtaining a 3D image of the semiconductor package; determining a distance S of the shadow and the bonded wire in the image; and obtaining a wire loop height H of the bonded wire.

5 Claims, 5 Drawing Sheets

Figure 1

(52) U.S. Cl.
CPC ..... *G01N 21/952* (2013.01); *H01L 21/67288* (2013.01); *H01L 22/12* (2013.01); *H01L 24/48* (2013.01); *G01N 21/95* (2013.01); *H01L 2224/4809* (2013.01); *H01L 2224/48227* (2013.01); *H01L 2924/00014* (2013.01); *H01L 2924/181* (2013.01)

(58) Field of Classification Search
CPC ........... G01N 22/04; G01N 2333/5428; G01N 24/081; G01N 33/5023
See application file for complete search history.

(56) References Cited

U.S. PATENT DOCUMENTS

| | | | | |
|---|---|---|---|---|
| 5,249,035 A | * | 9/1993 | Yamanaka | G01B 11/245 348/135 |
| 5,347,362 A | * | 9/1994 | Sugawara | G01N 21/95684 356/625 |
| 5,369,492 A | * | 11/1994 | Sugawara | G01N 21/8806 348/126 |
| 5,394,246 A | * | 2/1995 | Sugawara | G01N 21/8806 348/131 |
| 5,396,334 A | * | 3/1995 | Sugawara | G01N 21/8806 348/126 |
| 5,576,828 A | * | 11/1996 | Tomiyama | G01N 21/95684 250/559.34 |
| 5,583,641 A | * | 12/1996 | Tomiyama | G01N 21/88 250/559.34 |
| 6,118,540 A | * | 9/2000 | Roy | G01N 21/88 29/759 |
| 7,551,272 B2 | | 6/2009 | Vodanovic | |
| 7,573,569 B2 | | 8/2009 | Puah et al. | |
| 2005/0094865 A1 | * | 5/2005 | Cheng | G01B 11/026 382/146 |
| 2008/0204732 A1 | | 8/2008 | Vodanovic | |

* cited by examiner

APPARATUS AND METHOD FOR INSPECTING A SEMICONDUCTOR PACKAGE

CLAIM FOR PRIORITY

The present application is a national stage filing under 35 U.S.C. § 371 of PCT application number PCT/SG2014/000527, having an international filing date of Nov. 10, 2014, which claims priority to Singaporean application number 201308497-5, having a filing date of Nov. 11, 2013, the disclosures of which are hereby incorporated by reference in their entireties.

FIELD OF INVENTION

The invention relates to an apparatus and method for inspecting a semiconductor package.

BACKGROUND

Die and wire bonding is the most common interconnect technology employed in the electronic packaging industry. In recent years, new packaging trends have led to, for example, increases in the number of interconnections, circuit miniaturization, increased speed of assembly, reduced cost per interconnection and the like.

It should be noted that interconnection quality affects the quality of an end product. As the number of interconnections increases, the probability of producing a defective component also increases. Given that die and wire bonding typically occurs at a downstream stage of a semiconductor production process, the cost of a defective product due to a bad interconnect is high relative to a defective product which is detected at an early stage of the production process. It is currently possible to measure a height of bonded wires. This is also known as loop height. It is also possible to carry out inspection for the quality of the die/wire bonding as well as the integrity of die/wire/substrate after the bonding process.

Typical inspection methods for wire bonding (especially in the wire profile area) are usually carried out either manually (for example, visual check with a microscope, contact inspection and the like) or in a semi-automated manner. Such inspection methods are unfortunately slow, labour intensive, costly, and also prone to suffer physical damage due to contact and/or electrostatic damage. Moreover, manual inspection methods (for example, visual inspection with/without use of a sensor) are flawed due to human limitations, and are highly subjective and dependent on a human inspector.

Hence, there is clearly a need for improvements pertaining to inspection methods for wire bonding.

SUMMARY

In a first aspect, there is provided an apparatus for inspecting a semiconductor package. The apparatus includes at least one 3D camera positioned at a first angle relative to a normal axis of the semiconductor package; and a light source configured to provide illumination for the at least one 3D camera, the light source being directed at the semiconductor package. It is preferable that the at least one 3D camera and the light source are arranged in a fixed configuration relative to one another in the apparatus. The at least one 3D camera can be configured to be pivoted about a co-axial axis of an imaging lens.

Preferably, the light source is positioned at a second angle relative to the normal axis, opposite to the at least one 3D camera. It is preferable that the first angle and the second angle are acute angles. In addition, the light source may be transmitted through a small angular aperture. It is preferable that either the at least one 3D camera or a separate data processing device is configured to carry out image processing. The apparatus may also be rotatable about the normal axis.

The apparatus may further include a 2D camera; and an illumination module configured to provide illumination for the 2D camera. The 2D camera can be either an area scan camera or a line scan camera. It is preferable that the illumination module is configured to generate different lighting techniques at different wavelengths. The 2D camera can be configured to be pivoted about a co-axial axis of an imaging lens.

In a second aspect, there is provided a method for inspecting a semiconductor package. The method includes casting a shadow of a bonded wire onto the semiconductor package; obtaining a 3D image of the semiconductor package; determining a distance S of the shadow and the bonded wire in the image; and obtaining a wire loop height H of the bonded wire.

It is preferable that a plurality of the distance S is determined to compute a height profile of the bonded wire.

It is also preferable that the 3D image is obtained using a 3D camera positioned at a first angle $\beta$ relative to a normal axis of the semiconductor package, and the shadow is cast using a light source positioned at a second angle $\alpha$ relative to the normal axis, opposite to the 3D camera. The wire loop height H is $S \cdot \cos(\alpha)/\sin(\alpha+\beta)$.

In a final aspect, there is provided an apparatus including at least one 3D camera and at least one light source, the apparatus being for inspecting a semiconductor package while carrying out the aforementioned method.

DESCRIPTION OF FIGURES

In order that the present invention may be fully understood and readily put into practical effect, there shall now be described by way of non-limitative example only preferred embodiments of the present invention, the description being with reference to the accompanying illustrative figures.

DESCRIPTION OF PREFERRED EMBODIMENTS

The present invention provides an apparatus and method for inspecting a post wirebond package 20 (as shown in FIG.

1) which is effective, reliable, measurement-driven, and capable of identifying all die and wire-bond failure defects. In addition, the present invention is also capable of including measurement and inspection of other electronic components at a speed which is able to keep up with production processes while inspecting all products of the production process. It should be appreciated that the post wirebond package 20 can also be deemed to be a semiconductor package.

Figure 1:
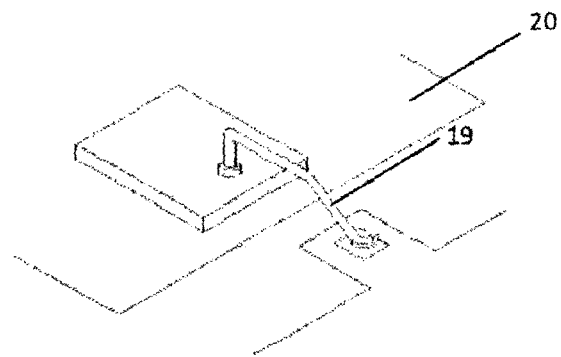
FIG. 1 shows an image of a bonded wire from die to substrate.
Figure 2:
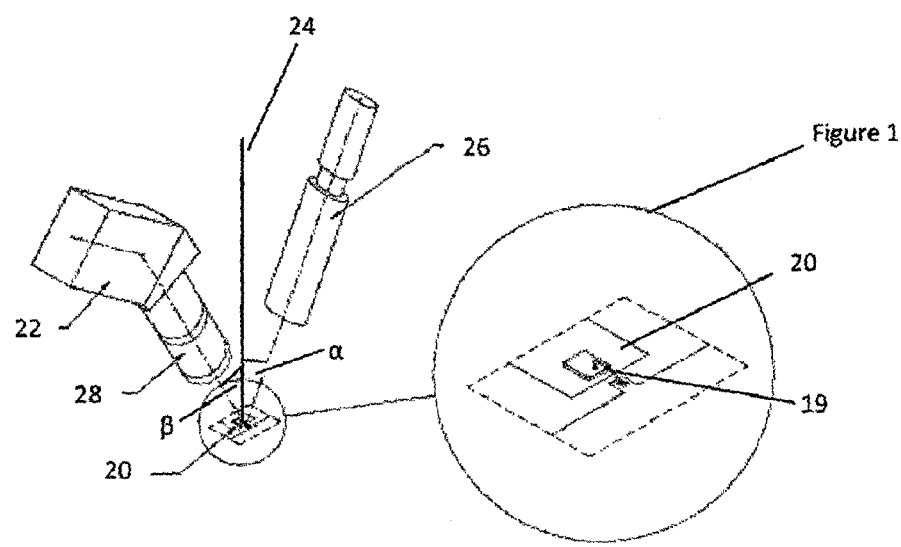
FIG. 2 shows a simplified view of a camera-lighting apparatus to create and image a shadow of a bonded wire.
Figure 8:
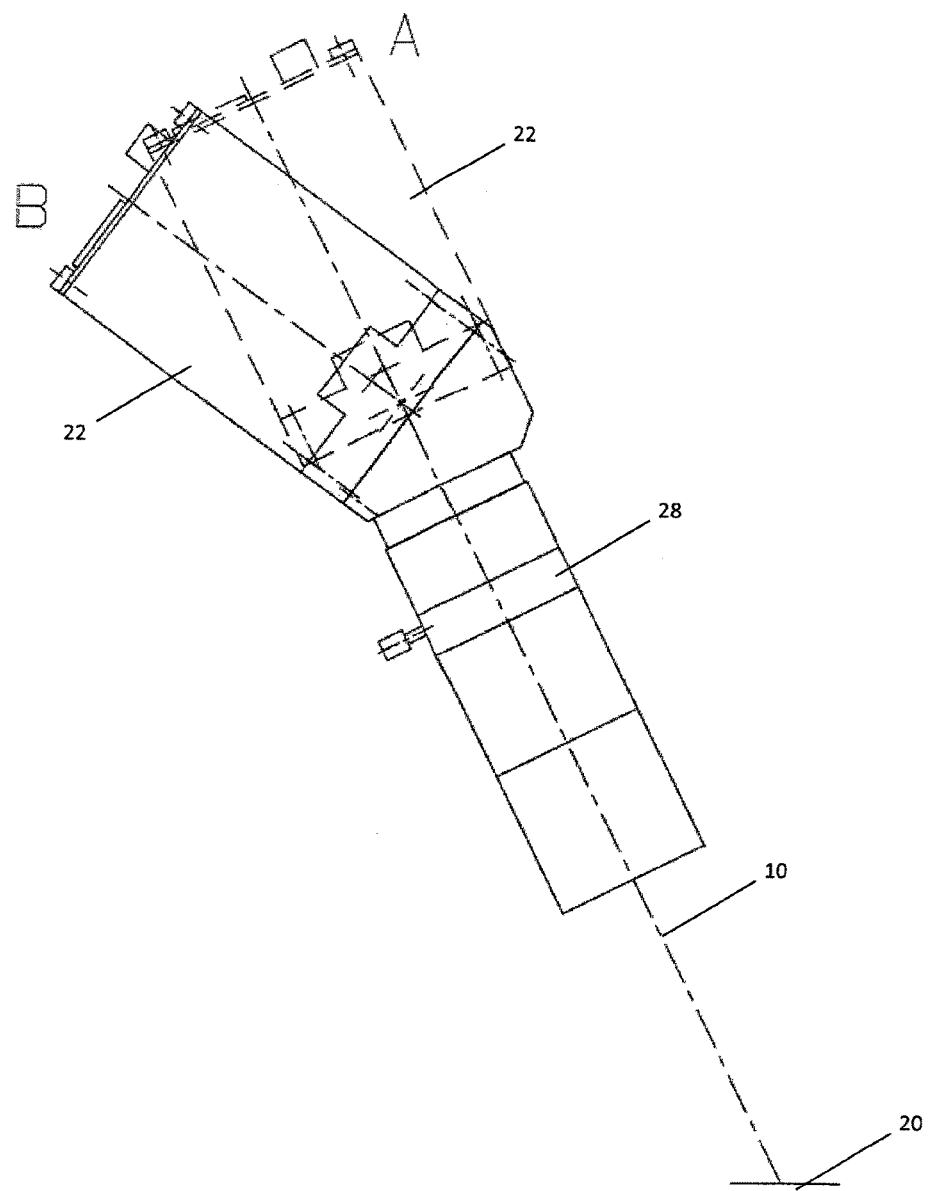
FIG. 8 shows a simplified view of a 3D camera pivoting about a co-axial axis of an imaging lens.

Referring to FIG. 2, there is shown a simplified setup for casting and imaging a shadow of a wire 19 in a wirebond package 20. There is provided a 3D camera 22 positioned at a first acute angle β measured from a normal axis 24 of the wirebond package 20. It is appreciated that the normal axis 24 is an axis which is perpendicular to the wirebond package 20, regardless of orientation of the wirebond package 20. In addition, there is also provided a light source 26 positioned at a second acute angle α measured from the normal axis 24 at an opposite side of the normal axis 24 compared to the 3D camera 22. The light source 26 is for illuminating the wirebond package 20. The light source 26 can be of a type selected from, for example, telecentric, parallel, quasi-parallel light, single spot illumination and so forth. Illumination from the light source 26 is used to cast a shadow of the wire 19 on the substrate and the illumination is reflected off the wirebond package 20 and goes back to the camera 22 through imaging lens 28. Referring to FIG. 8, the camera 22 may be tilted about a coaxial axis 10 of lens 28 to obtain an in-focus full field of view (FOV) of package 20 according to Scheimpflug principle. Tilt parameters for the camera 22, such as, for example, angle of tilt, distance from lens, and the like will depend on user requirements for parameters of the captured image, such as, for example, optical resolution, image quality, and the like. For the sake of illustration, the camera 22 is shown to be in a first position of "A" and subsequently moved to a second position of "B" so as to obtain a desired in-focus full field of view of package 20.

Having the 3D camera 22 positioned at the first acute angle β allows the 3D camera 22 to capture appropriate images regardless of surface finish of the wirebond package 20. If the 3D camera 22 is positioned directly above the wirebond package 20 with light coming from the side, the 3D camera 22 will be able to capture shadows but not when the surface of the wirebond package 20 has a mirror finish. Moreover, when the 3D camera 22 is located directly above the wirebond package 20, it is not able to capture light reflected from the wirebond package 20 if its surface has a mirror finish. By inclining the 3D camera 22, wires bonded in different directions can also be assessed.

Figure 3:
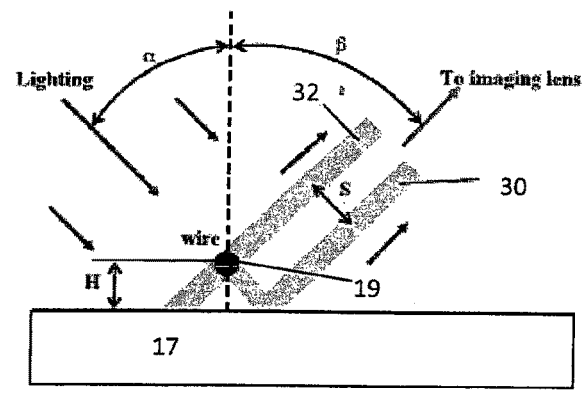
FIG. 3 shows a simplified view of how a shadow of a bonded wire is created and imaged.

FIG. 3 is a simplified view of how a shadow of a bonded wire is created and imaged. The positioning of the 3D camera 22 and the light source 26 enables the casting and imaging a shadow of a wire 19 in a wirebond package 20, and consequently allows the computation of a wire height of the wire 19. A wire loop height H of the wire 19 is shown. A shadow of the wire 19 is cast on a substrate 17 (part of the wirebond package 20) using illumination from the light source 26 placed at the first acute angle α measured from the normal axis 24 of the substrate 17. A first image 30 of the wire shadow and a second image 32 of the wire 19 are captured by the 3D camera 22 which is positioned at the second acute angle β measured from the normal axis 24 of the substrate 17. A small angular aperture is used with the light source 26 so as to obtain a high contrast of the wire shadow on the substrate 17.

Figure 7:
FIG. 7 shows a sample 3D image obtained using a camera-lighting apparatus of the present invention.

The images 30, 32 are two separate portions of a common image that is captured by the 3D camera 22. Typically the common image is bright field with 2 dark strips which correspond to the wire image 32 and wire shadow image 30. FIG. 7 shows a sample common image which includes the images 30, 32 for a typical wirebond package 20. The distance S between the two dark strips corresponds to wire 19 position above the substrate 17. Referring to FIG. 7, a left portion of the image is more sharply focussed compared to a right portion of the image. In order to get the full FOV in focus, the camera will have to be tilted relative to an optical axis of an imaging lens.

An image processing analysis of the common image can measure the distance S between centres of the wire image 32 and wire shadow image 30 (as shown in FIG. 3). The image processing analysis can be carried out by using proprietary software which includes use of algorithms to determine the distance S. The image processing analysis can be carried out either in the 3D camera 22 or in a separate data processing device. The wire loop height (H) above the substrate 17 is calculated by:

$$H = S \cdot \cos(\alpha)/\sin(\alpha+\beta) \quad (1)$$

where α and β are as per the earlier described angles.

Typically, α≠β if the substrate 17 has a matte surface while α=β if the substrate 17 has shiny/mirror-like surface. Depending on surface finishes, the 3D camera 22 and the light source 26 are arranged such that the 3D camera 22 is able to image the shadow and actual wire within a field-of-view of the 3D camera 22. Given that the substrate surface may have different finishes such as, for example, matt, semi-matt, glossy, mirror and so forth, α=β even if the substrate 17 has a matte/semi-matte surface.

When α=β, equation (1) can be simplified to be:

$$H = S/(2 \cdot \sin(\alpha)) \quad (2)$$

Thus, when α=β=45°, $$H = S \cdot 0.707 \quad (3)$$

Thus, in an instance when α=β=45°, the wire loop height H can be calculated by determining a value of S. The wire position above the substrate may vary along length of the wire and as a result, the resultant distance S will vary accordingly. The image processing software will analyse the distance S along the wire. The image processing software is able to process the image and obtain a plurality of S for each wire. By obtaining the plurality of "S-es" (and with known angles), the image processing software will be able to compute a height profile of the wire.

The wire loop height H is a critical aspect of wirebond packages because it affects both performance and reliability of the packages. The loop height H cannot be too high because this can result in an exposed wire(s) during molding. Moreover, even if the wire(s) is not exposed, high loops can lead to long and sagging wires that are prone to being swept along in a direction of flow of a molding compound during encapsulation. This can lead to shorting of the wires. Furthermore, unnecessarily long wires also lead to degradation of electrical performance because of cross-talk between the wires.

Conversely, a low wire loop height H is undesirable as it may indicate that the wire is too taut, whereby substantial stresses has been and is being exerted on a neck or heel of the bond. These stresses can lead to neck or heel cracks/breaks, which generally leads to failure of the wirebond package 20. In addition, a low wire loop height H can result in contact between the wire and the wirebond package 20, which leads to a faulty/non-functional package 20.

Generally, the assessment of wire loop heights is carried out in a scale of microns, and a nominal deviation of a pre-determined height such as, for example, more/less than fifteen to thirty microns of the pre-determined height will activate a "fail" notification. Exact wire loop height and the failing criteria depends on, for example, a type of semiconductor package, a type of packaging technology, a type of bonding, a diameter of wire, user's production process, end-product requirements, and so forth. It is appreciated that the present invention is able to measure wire loop height up to a range of five to six microns in accuracy and repeatability.

It should be appreciated that more than one wire 19 of the wirebond package 20 can be analysed simultaneously. In such instances, the common image will include multiple pairs of the images 30, 32. The image processing software can analyze all pairs to measure the respective S, and correspondingly providing H of the wire 19.

A 2D camera and illumination module combination can be used to identify defects of the wirebond package 20. The illumination module will depend on a pre-defined defects list and quality requirement. The illumination module can be configured to generate different lighting techniques at different wavelengths to allow different sets of image data to be generated during operation to provide the requisite contrast to identify defective conditions of the wirebond package 20. The type of defective conditions which can be identified include, for example, scratched die, cracked die, die misalignment, absent die, epoxy coverage/spread, epoxy measurement, absence/presence of wire, wire connection issues, damaged wires, wire mis-alignment, damaged substrate, bent substrate, and so forth. Typically, the 2D camera is placed perpendicular to the wirebond package 20. However, the 2D camera may sometimes be positioned at an inclined configuration at an angle which depends on both the wire profile and the surface finishes. It should be appreciated that positioning the 2D camera at an inclined configuration may also involve pivoting of the 2D camera about an imaging lens to obtain an in-focus full field of view of package 20 according to Scheimpflug principle. The Illumination module for the 2D camera typically consists of coaxial lighting and/or ring lighting.

The 2D camera can be either an area scan camera or a line scan camera which is configured to move about to capture an image of an entire substrate surface and all wires either on-the-fly (during the production process for the wirebond package 20) or start-stop method (of the production process for the wirebond package 20). The 2D camera is configured to move about as an orientation of bonded wires in the wirebond package 20 varies with production process and device types. Most wires are bonded in an orientation from die to substrate in an X and/or Y axes but there is also a subset of packaging that includes bonded wire in more than X and/or Y axes.

Figure 4:
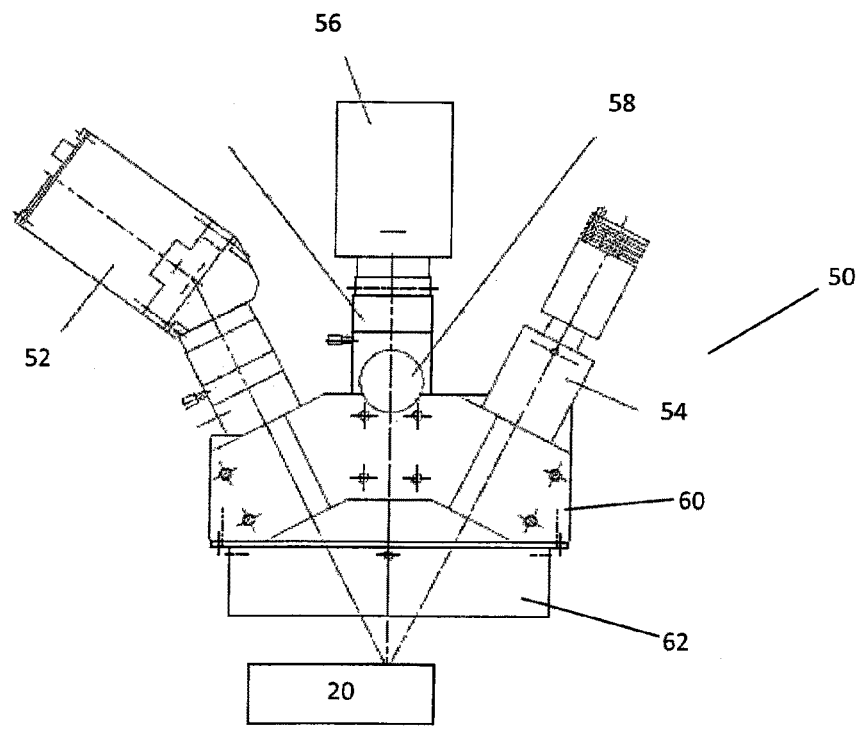
FIG. 4 shows a front view of a first embodiment of a camera-lighting apparatus of the present invention.
Figure 5:
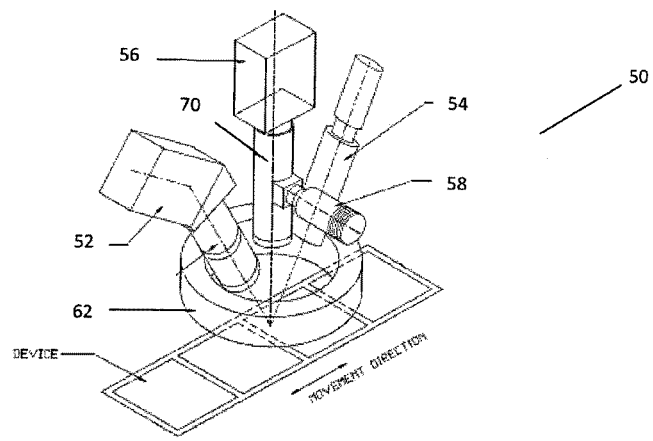
FIG. 5 shows a perspective view of main components of the first embodiment of a camera-lighting apparatus of FIG. 4.

Referring to FIGS. 4 and 5, there is shown a first embodiment of an apparatus 50 for inspecting at least one post wirebond package. The apparatus 50 includes a first 3D camera 52 and a light source 54 for the first 3D camera 52. In addition, the apparatus 50 also includes a second 2D camera 56 and an illumination module 58 for the second 2D camera 56. The apparatus 50 includes a casing 60 for containing components of the apparatus 50, and the casing 60 also ensures that the components of the apparatus 50 are arranged in a fixed configuration relative to each other. It should be noted that the first 3D camera 52 and the light source 54 are arranged in a fixed configuration to enable the casting and imaging a shadow of a wire in a wirebond package as described in an earlier paragraph of the description, while the second 2D camera 56 and the illumination module 58 are arranged in a fixed configuration to identify defective conditions of the wirebond package as described in an earlier paragraph of the description. The apparatus 50 also includes an optional (depends on user requirements) ringed light source 62 for providing circular illumination for the wirebond packages.

It should also be appreciated that the apparatus 50 can be configured to be rotatable about a normal axis 70 such that the casting and imaging of a shadow of a wire in a wirebond package can be carried out regardless of orientation of the wire as the wires can be bonded in different directions. It is possible to employ a plurality of 3D cameras to cater for different directions of the bonded wires which would improve speed of package inspection compared to the speed of the rotatable apparatus 50. However, the use of the plurality of 3D cameras is not cost effective.

Figure 6A:
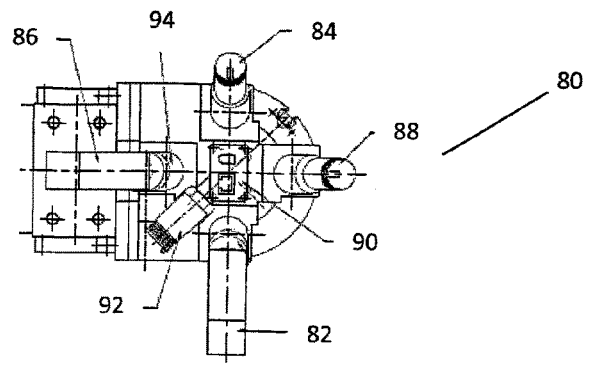
FIGS. 6a-c shows a top, front and rear view of a second embodiment of a camera-lighting apparatus of the present invention.
Figure 6B:
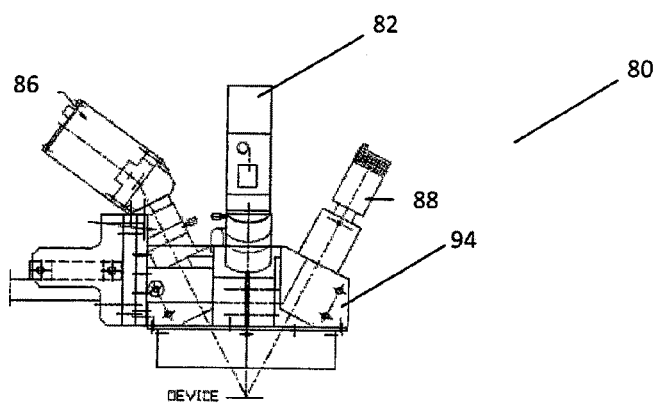
Figure 6C:
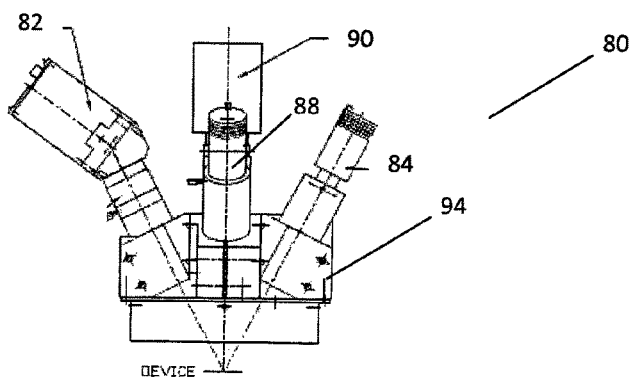

Referring to FIG. 6, there is shown a second embodiment of an apparatus 80 for inspecting at least one post wirebond package. The apparatus 80 includes a first 3D camera 82 and a first light source 84 for the first 3D camera 82. In addition, the apparatus 80 also includes a second 3D camera 86 and a second light source 88 for the second 3D camera 86. Furthermore, there is also a third 2D camera 90 and an illumination module 92 for the third 2D camera 90. The apparatus 80 includes a casing 94 for containing components of the apparatus 80, and the casing 94 also ensures that the components of the apparatus 80 are arranged in a fixed configuration relative to each other. It should be noted that the 3D cameras 82, 86 and their respective light sources 84, 88 are arranged in a fixed configuration such that each 3D camera-light source pairing is able to cast and image a shadow of a wire in a wirebond package as described in an earlier paragraph of the description. Moreover, the 3D cameras 82, 86 and their respective light sources 84, 88 are able to operate independently in their respective pairings. The respective pairings are helpful during instances where one 3D camera and its accompanying light source are unable to obtain a value of S due to an orientation of the wire, and as such, another pairing of 3D camera and light source is needed. In addition, the third 2D camera 90 and the illumination module 92 are arranged in a fixed configuration to identify defective conditions of the wirebond package as described in an earlier paragraph of the description. It should also be appreciated that the apparatus 80 can be configured to be rotatable about in a manner similar to the first embodiment such that the casting and imaging of a shadow of a wire in a wirebond package can be carried out regardless of orientation of the wire.

It should be appreciated that the apparatus 50/80 is of compact design dimensions and can be arranged in a circular configuration. The apparatus 50/80 allows for 2D imaging for inspection of defects and 3D imaging for die height/wire profile measurements of die and/or wirebond process at a single station which does not require manual intervention. Moreover, the apparatus 50/80 also enables on-the-fly inspection of wirebond packages to improve the throughput of an inspection system. In addition, the apparatus 50/80 also allows high precision and high-speed inspection for 100% inspection of post-die or post-wire bonding processes. The apparatus 50/80 can be a standalone QA system, or can be integrated with other equipment. In this regard, the apparatus 50/80 is able to automate and improve upon the tedious manual process of inspection of wirebond packages.

Whilst there have been described in the foregoing description preferred embodiments of the present invention, it will be understood by those skilled in the technology concerned that many variations or modifications in details of design or construction may be made without departing from the present invention.

The invention claimed is:

1. A method for inspecting a semiconductor package, the method including:
   casting a shadow of a bonded wire onto the semiconductor package;
   obtaining a 3D image of the semiconductor package;
   determining a distance S of the shadow and the bonded wire in the image; and
   obtaining a wire loop height H of the bonded wire.

2. The method of claim 1, wherein a plurality of the distance S is determined to compute a height profile of a length of the bonded wire.

3. The method of claim 1, wherein the 3D image is obtained using a 3D camera with an imaging lens positioned at a first angle $\beta$ relative to a normal axis of the semiconductor package.

4. The method of claim 3, wherein the shadow is cast using a light source positioned at a second angle $\alpha$ relative to the normal axis, opposite to the 3D camera.

5. The method of claim 4, wherein the wire loop height H is $S \cdot \cos(\alpha)/\sin(\alpha+\beta)$.

* * * * *